United States Patent
Williams

(10) Patent No.: US 6,493,577 B1
(45) Date of Patent: Dec. 10, 2002

(54) METHOD AND SYSTEM FOR DETECTING WHITE MATTER NEURAL INJURY AND PREDICTING NEUROLOGICAL OUTCOME PARTICULARLY FOR PRETERM INFANTS

(75) Inventor: Christopher Edward Williams, Grafton (NZ)

(73) Assignee: Auckland Uniservices Ltd., Auckland (NZ)

( * ) Notice: Subject to any disclaimer, the term of this patent is extended or adjusted under 35 U.S.C. 154(b) by 0 days.

(21) Appl. No.: 09/509,186

(22) PCT Filed: Sep. 23, 1998

(86) PCT No.: PCT/NZ98/00142
§ 371 (c)(1), (2), (4) Date: Apr. 7, 2000

(87) PCT Pub. No.: WO99/15067
PCT Pub. Date: Apr. 1, 1999

(30) Foreign Application Priority Data

Sep. 23, 1997 (NZ) ................................................ 328820

(51) Int. Cl.[7] .............................................. A61B 5/00
(52) U.S. Cl. ...................................................... 600/544
(58) Field of Search ................................. 600/544, 545

(56) References Cited

U.S. PATENT DOCUMENTS

| 4,753,246 A | 6/1988 | Freeman ..................... 128/731 |
| 4,907,597 A | 3/1990 | Chamoun ................... 128/731 |
| 5,230,346 A | 7/1993 | Leuchter et al. ............ 128/731 |
| 5,269,315 A | * 12/1993 | Leuchter et al. ............ 600/544 |
| 5,309,923 A | 5/1994 | Leuchter et al. ............ 128/731 |
| 5,458,117 A | 10/1995 | Chanoun et al. ............ 128/734 |
| 5,807,270 A | 9/1998 | Williams |
| 6,052,619 A | * 4/2000 | John ........................... 600/544 |

OTHER PUBLICATIONS

Williams, et al, "Outcome after Ischemia in the Developing Sheep Brain: and Electorencephalographic and Histological Study", *Annals of Neurology*, vol. 31, No. 1 Jan. 1992, pp. 14–21.

* cited by examiner

Primary Examiner—Robert L. Nasser
(74) Attorney, Agent, or Firm—Fliesler, Dubb, Meyer & Lovejoy LLP

(57) ABSTRACT

A method for detecting white matter neural injury and predicting neurological outcome for a patient, comprises acquiring EEG signal(s) from the surface of the head of the patient, and analyzing the frequency distribution or content of the signal(s) to produce output information indicative of cerebral white matter injury for the patient. Loss or reduction of activity in the upper portion or spectral edge of the EEG frequency domain particularly in the immature brain is predictive of neural dysfunction. A system for detecting white matter neural injury and predicting neurological outcome for a patient is also described.

20 Claims, 11 Drawing Sheets

METHOD AND SYSTEM FOR DETECTING WHITE MATTER NEURAL INJURY AND PREDICTING NEUROLOGICAL OUTCOME PARTICULARLY FOR PRETERM INFANTS

FIELD OF INVENTION

The invention comprises a method and apparatus for detecting neural injuries and predicting neurological outcome. In particular the invention is useful for detecting injuries to the immature cerebral white matter in preterm infants and for enabling rapid prediction of the development of subtle and severe lesions in the cerebral white matter of and neurological outcome for preterm infants.

BACKGROUND TO THE INVENTION

Very premature infants have a markedly increased risk of neurological morbidity (Volpe, Prev. Med., 23: 638–645, 1994). A recent study using cranial ultrasonography revealed that only 2% of infants (at 23 weeks), 21% (at 24 weeks) and 69% (at 25 weeks) survived without severe abnormalities (Allen et al., New Eng. J. Med, 329: 1597–1601, 1993). White matter brain damage is a characteristic of these injuries. Patterns of damage range from subtle gliosis (telencephalic leukomalacia) through to severe cystic infarctions of the periventricular and subcortical white matter (Volpe, Prev. Med., 23: 638–645, 1994).

Histopathologic studies indicate some of these lesions develop prenatally, others postnatally. Poor neurological outcome is associated with the presence of these white matter injuries (Guit et al., Radiology, 175: 107–109, 1990). The severe periventricular lesions are strongly associated with cerebral palsy (Hoon, J. Perinatol., 15: 389–394, 1995).

Long term neurological outcome appears to be similarly compromised. In a group of less than 32 week old premature infants at the age of 9 years 19% were in special education, 32% were in a grade below the appropriate level for their age and 38% required special assistance (Hille et al., J Pediatr., 125: 426–434, 1994).

Similarly, another study has shown that in very premature infants about 5–15% develop major spastic motor deficits and an additional 25–50% exhibit developmental and cognitive disabilities (J. J. Volpe. Brain injury in the premature infant—Current concepts of pathogenesis and prevention. *Biol Neonate* 62:231–242, 1992).

The aetiology of these lesions is not completely understood (Armstrong, Semin. Perinatol., 17: 342–350, 1993), but are thought to occur secondary to various prenatal environmental and genetic factors (Lou, Brain Dev., 16: 423–431, 1994).

Cerebral hypoperfusion is considered to be a significant final common pathway in the pathogenesis of these encephalopathies (Lou, Brain Dev., 16: 423–431, 1994). Experimental and epidemiological studies generally support this hypothesis. For example, intrapartum acidosis and asphyxia in the premature infant carry a high risk of periventricular leukomalacia (Low et al., Am. J. Obstet. Gynaecol., 162: 977–981, 1990). Also, both increased levels of hypoxanthine and prolonged metabolic acidosis in the neonatal period are associated with a high risk of periventricular lesions (Russel et al., Arch. Dis. Child., 67: 388–392, 1992; Low et al., Am. J. Obstet. Gynaecol., 162: 977–981, 1990). In particular, periventricular lesions are probably caused by cerebral hypoxia-ischaemia following arterial hypotension (Iida et al., Pediatr. Neurol., 8: 205–209, 1992). Cerebral hypoxia-ischaemia may arise from problems associated with prematurity including respiratory distress syndrome, patent ductus arteriosis, necrotizing enterocolitis and sepsis. There is considerable variation in the pattern of lesions observed and a range of factors are likely to influence outcome, including gestational age and the severity and nature of the insult (Gluckman et al., Proceedings of The Alfred Benzon Symposium no. 37, Munksgaard, Copenhagen, 1993). Other factors such as hypoglycaemia, infections or toxaemia are also likely to be important (Piekkala et al., Early Hum. Dev., 13: 249–268, 1986).

Current methods for assessing brain injury reveal damaged areas of the brain, but do not identify those premature infants at risk of suffering a neural injury. Brain damage assessed by neurological examination is of limited prognostic value, especially for those preterm infants on life support. Ultrasonography is also used and reveals lesions as white matter echodensities and echoluciencies, which are useful in predicting future handicap, such as cerebral palsy. However, this approach is less suitable for monitoring and detecting pathophysiologic events which may occur over several days, the knowledge of which could be used to minimise or avoid further injury.

Greater reliance needs to be placed on other investigations such as pathophysiologic measures (Hill, Clin. Invest. Med., 16: 141–148, 1993). Doppler cerebral haemodynamic measures have not been proven to be predictive of outcome (Shortland et al., J. Perinat. Med., 18: 411–417, 1990). In the more mature brain the EEG signal can be used to predict severe loss of the superficial neurons that generate this signal (Williams et al Ann Neurol, 31:14–21 1992).

Two patterns of white matter damage can occur: 'subtle' white matter damage which manifests as gliosis, impaired myelination, ventriculomegaly and is often termed telencephalic leucomalacia; 'severe' cystic infarctions within the perventricular and subcortical white matter. The former are associated with cognitive deficits and the latter lesions are strongly associated with cerebral palsy.

Histopathological studies indicate the timing of injury is variable—some may develop prenatally whereas many others appear to develop during the first postnatal weeks. However in surviving infants the timing of injuries is typically unclear and there are considerable problems with detecting when these white matter injuries occur (D. J. Murphy, M. V. Squier, P. L. Hope, S. Sellers and A. Johnson. Clinical associations and time of onset of cerebral white matter damage in very preterm babies. *Arch Dis Child Fetal Neonat Ed* 75 (1 Special Issue SI):F 27-F 32, 1996). The inability to detect the onset of injury makes management difficult. For example, if a subtle or severe injury to the deep white matter could be rapidly detected, then the injurious factor could be corrected or treatment applied.

SUMMARY OF THE INVENTION

The invention provides a method and system for detecting white matter neural injury and predicting neurological outcome particularly in preterm infants.

In broad terms in one aspect the invention comprises a method for detecting white matter neural injury and predicting neurological outcome for a patient, comprising:

acquiring EEG signal(s) from the surface of the head of the patient, and analysing the frequency distribution of the signal(s) to produce output information indicative of cerebral white matter injury for the patient.

Preferably the method includes comparing the analysed data with stored comparative spectral edge and neurological outcome information to produce information useful for managing the patient.

In broad terms in another aspect the invention comprises a system for detecting neural injury and predicting neurological outcome for a patient, comprising:

means for acquiring EEG signal(s) from the surface of the head of a patient, and computing means arranged to analyse the frequency distribution of the EEG signals to produce output information indicative of cerebral white matter injury for the patient.

An electroencephalogram or EEG provides a record of electrical activity from the most superficial layers of the cerebral cortex recorded from electrodes on the scalp. This activity is the result of the rhythmic discharging of neurons under the electrode. The EEG signal provides information about the frequency and amplitude of the neuronal electrical activity and its temporal variation. We have found experimentally that loss of spectral edge frequency is highly predictive of deep white matter damage in the preterm foetus. By preterm or premature is meant infants born at less than 37 weeks gestation. The method and system of the invention also have application in detecting white matter neural injury in child and adult patients however.

DESCRIPTION OF FIGURES

The invention is further described with reference to the accompanying figures in which:

FIG. 3a is a recording from a normal infant and FIG. 3b is a recording from an infant with cystic white matter lesions.

DETAILED DESCRIPTION

Figure 3A:
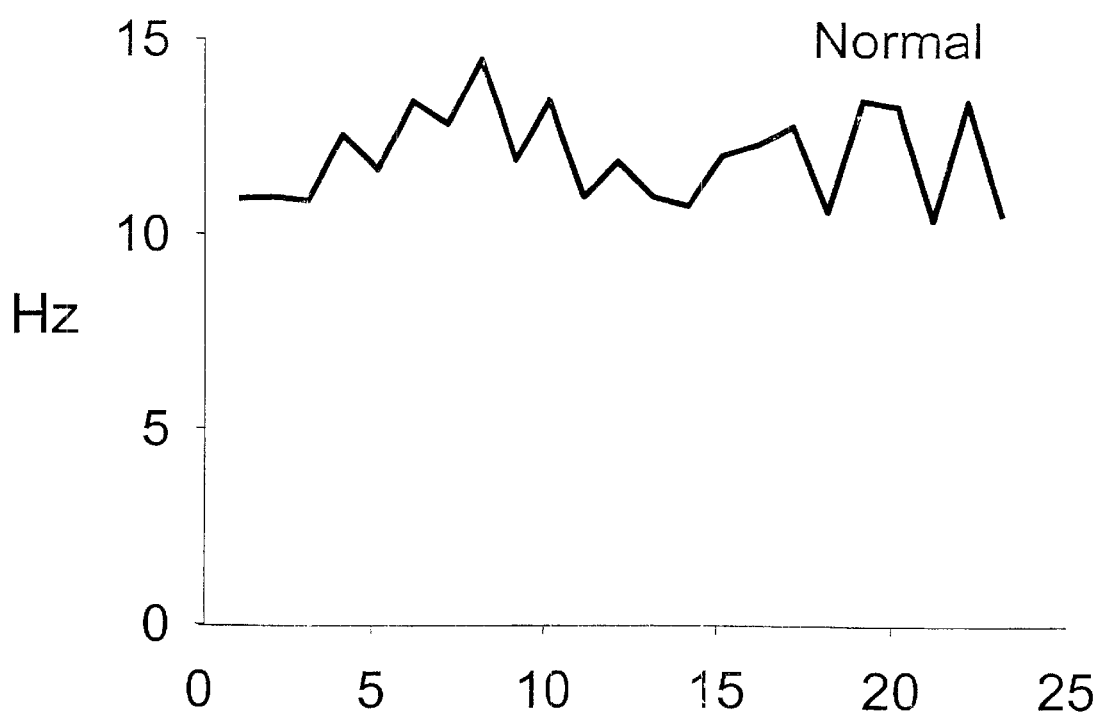
FIGS. 3a and 3b are graphs of EEG spectral edge frequency recordings for human infants.
Figure 3B:
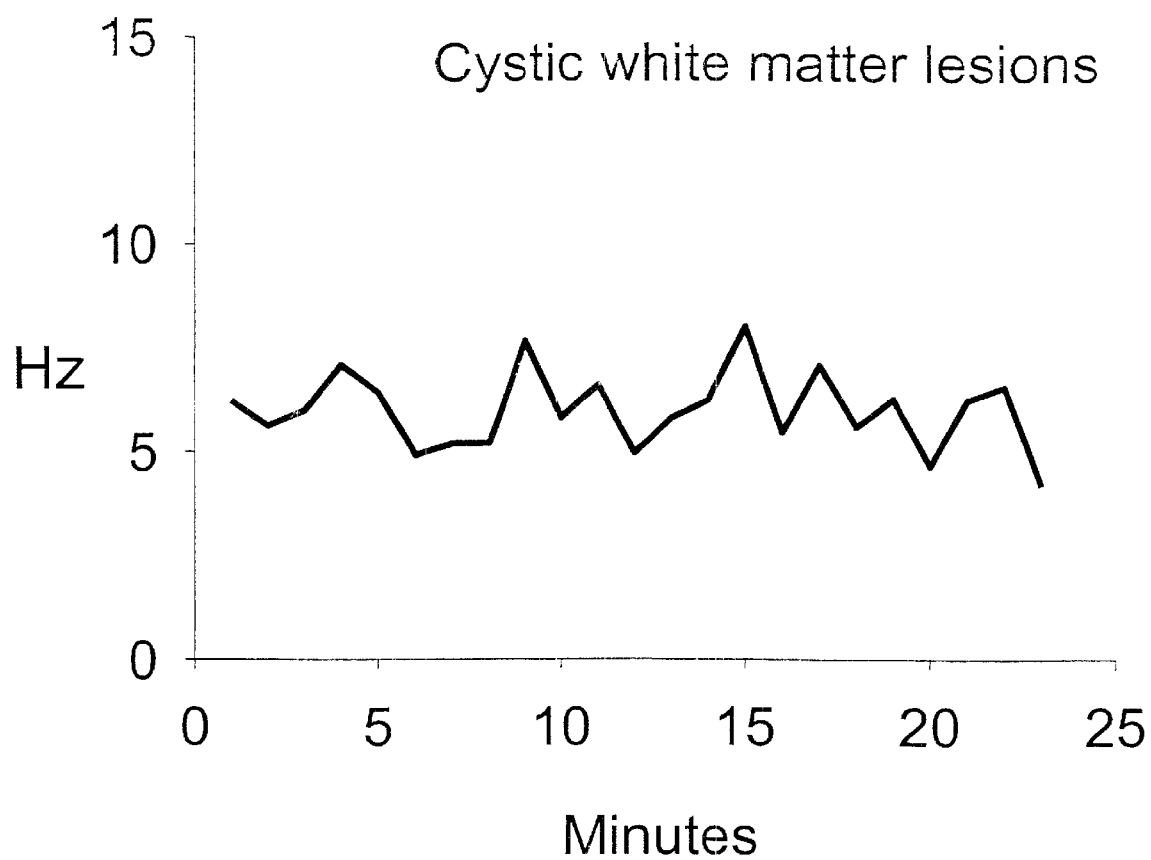

As stated we have found that a lowering of the frequency distribution of the EEG activity, measured by a fall in spectral edge frequency of the EEG signals, is indicative of cerebral white matter injury. Typically the EEG frequency spectrum comprises signals in a 1 to 20 Hz range, with most activity between about 1 and 15 Hz. In the method and system of the invention, the EEG signals are analysed to determine the proportion of the intensity spectrum in the top 50%, preferably the top 30%, more preferably the top 10%, and most preferably the top 5% of the frequency range, and a reduction in this spectral edge frequency is indicative of cerebral white matter both subtle and severe white matter injuries and long term neurological outcome. FIG. 3a shows EEG spectral edge recording for a normal human infant, with EEG activity up to about 15 Hz. FIG. 3b shows EEG spectral edge recording for an infant with cerebral white matter cystic lesions, in which there was a loss of frequency with spectral edge activity above about 10 Hz. These distinctive frequency responses are similar to those that were observed in the preterm fetal sheep.

Figure 2:
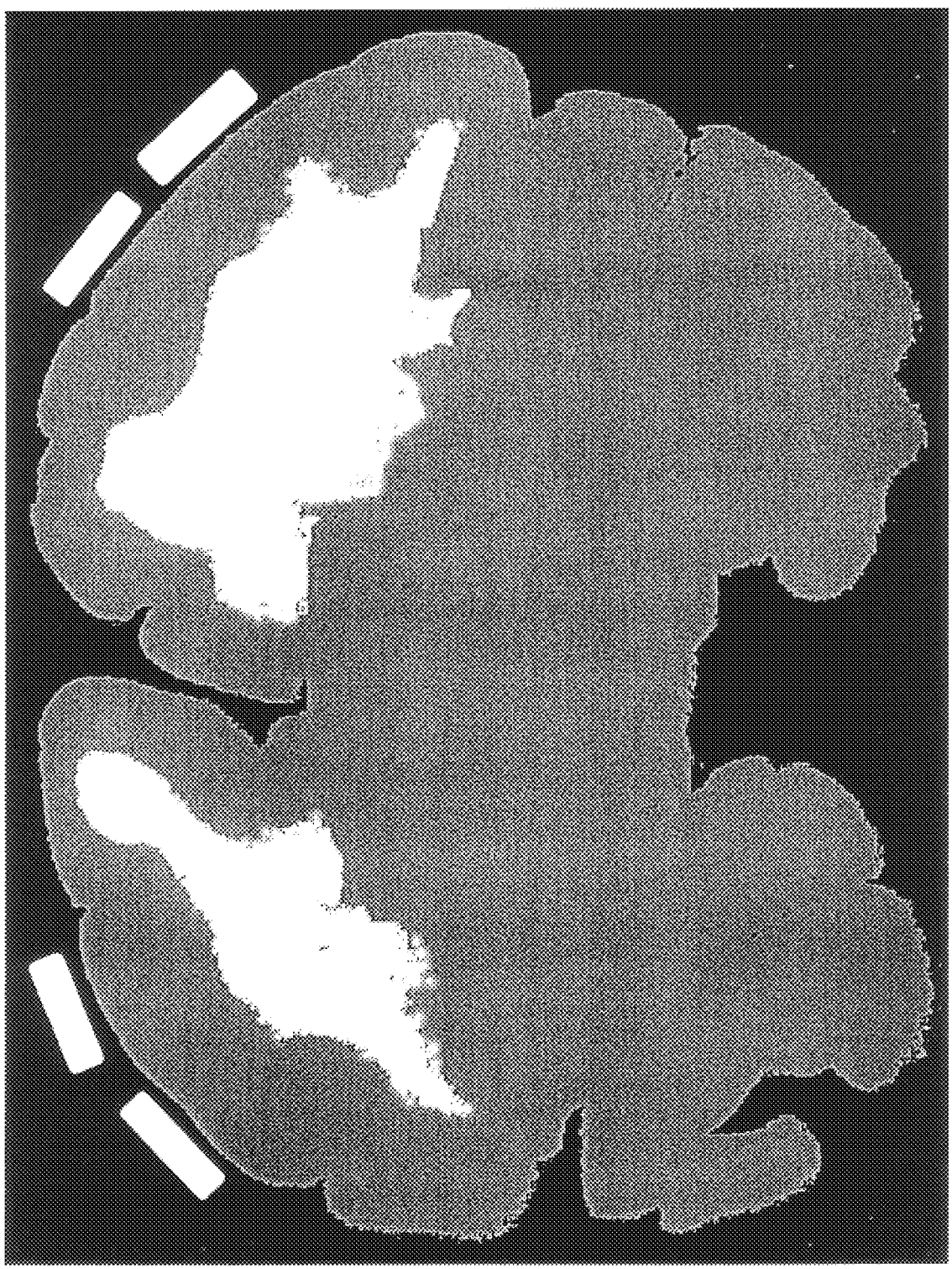
FIG. 2 is a schematic horizontal cross-sectional diagram of the brain showing where white matter injuries develop and the optimum placement of the EEG electrodes on each hemisphere for the detection of these injuries.

FIG. 2 is a schematic horizontal cross-sectional diagram of a preterm infant's brain showing the vulnerable developing white matter regions dorsal and lateral to the lateral ventricles. These regions may suffer 'subtle' injuries where gliosis occurs or develop more severe cystic lesions. Note that the overlying grey matter or neurons are typically spared from these injuries. FIG. 2 also shows the preferred EEG electrode placement with the system and method of the invention. A useful site is to record from the parasagittal region/fronto-parietal-occipital cortex that overlies the region where the white matter injury may develop as indicated in FIG. 2.

In the method and system of the invention a suitable conventional electrode, amplifier and patient isolation system is used to acquire EEG signals from the head of a subject patient such as an infant, which are then analysed in computing means comprising signal analysis software arranged to examine the upper portions or spectral edge of the frequency domain of the EEG signals, and to output the analysis as information indicative of neural injury and neurological outcome for the subject infant.

The system hardware may take any suitable form such as a personal computer including a dedicated data acquisition board to which a number of EEG electrodes are connected, the computer screen displaying the analysis graphically and/or as text. In another form an otherwise conventional EEG system may be arranged to process acquired EEG signals and analyse the signals according to the method of the invention, as a signal processing option on the EEG machine, and display and/or print the results. In a further form a system of the invention may comprise a smaller dedicated apparatus or instrument including EEG signal acquisition equipment, a computer section comprising an embedded microprocessor, data analysis software, and a display. In each case the results of the analysis may be displayed or printed for interpretation by a physician, or may be further processed against stored comparative information and displayed or printed in a form which is predictive of neurological outcome of the subject infant.

The EEG signals may be acquired from electrodes placed on the infant's head over the parasagittal region/fronto-parietal-occipital cortex. They may be acquired over a number of hours, or over one or more days, and may be averaged over such periods. They may be analyzed in the frequency domain for loss of EEG activity above about 10 Hz, or above about 8 Hz.

Figure 1:
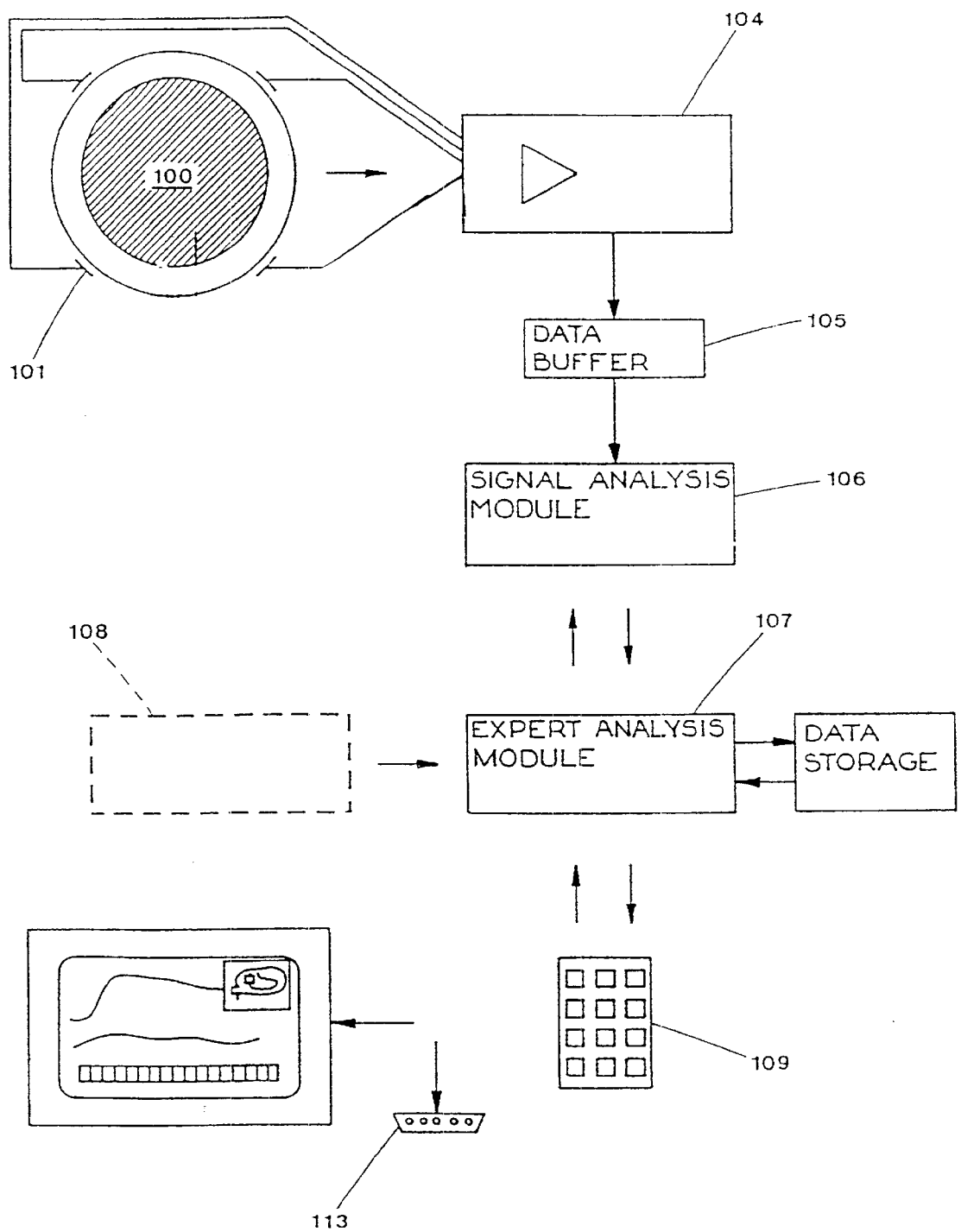
FIG. 1 is an overview of one form of system of the invention.

FIG. 1 schematically illustrates one form of system of the invention. A set of EEG leads are applied to the head 100 of an infant as shown at 101. The EEG signals are filtered as necessary, amplified, and analogue-to-digital converted in block 104 and passed to data buffer 105. The digitised input signals data may also be compressed and stored. Data compression may involve averaging or time-to-frequency domain conversion. Standard computer-compatible data storage devices with a standard system for file naming and configuration may be utilised.

The intensity spectrum of the EEG signals in the frequency domain is obtained using fast Fourier transform techniques (FFT) or any other signal processing technique which enables the frequency content of the EEG signals to be examined and measures of the frequency distribution such as spectral edge frequency to be calculated. The preferred form system is arranged to carry out this analysis in the signal analysis module 106. The results may then be displayed for interpretation by a physician, but preferably the current and stored data for the patient may be analysed against stored comparative information on spectral edge frequency versus likely neurological outcome and analytical rules indicated by block 108, in expert analysis module 107 and the results displayed.

Optionally the system may make available expert advice having an inbuilt ability to predict outcome and/or to identify the pathological processes taking place through an advisor/help system. The system may also make available representative examples of pathophysiologic reactions which can be called up by a user contemplating the case under study.

Once a loss of EEG activity in the upper part of the frequency range in an infant is detected by the system and method of this invention, therapy against the development of white matter injury may be applied to the infant.

FIG. 1 also comprises a dataflow diagram and illustrates that digital signals are fed continuously into input data buffer 105, subsequently through the signal analysis module 106, and then through the expert analysis module 107, and to the display, or data storage device(s). The signal analysis module also performs artefact rejection, and data reduction.

User interaction with and control of the system in the preferred form system may be via a touch sensitive screen or a touch panel or keypad 109, on the front face of an instrument for example, a keyboard and/or a mouse, a separate hand held infra-red unit, or other convenient form of input device. The unit may include a printer port 113 or a built-in printer, or a network interface. Preferably the system is capable of storing and recalling data over a period of for example 3 days or more.

Preferably the system monitors each signal line in order to confirm that each channel continues to provide reliable results because (for example) attached electrodes can be detached or lose effectiveness in other ways. In the event of a problem the corresponding data is disregarded and a warning message is generated, and the system may also indicate to the user any detached or ineffective electrode.

Figure 4A:
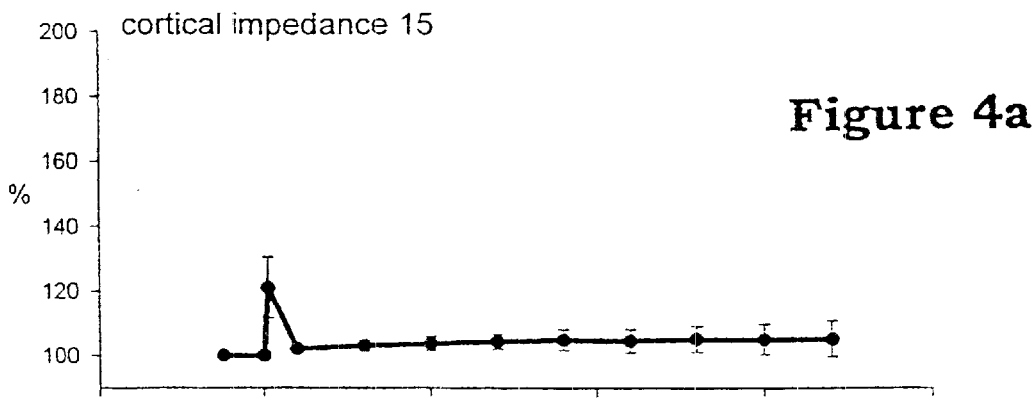
FIGS. 4a, 4b and 4c are graphs of cortical impedance for the preterm (0.65 gestation) foetal sheep over an 80 hour period following a 15, 22.5 and 30 minute cerebral hypoperfusion injury respectively.

The following description of experimental work further assists understanding of the invention:
Experimental In order to determine if any biophysical parameters were useful for detecting injuries within the immature white matter the following investigations were performed. Preterm 0.65 gestation foetal sheep were subjected to cerebral hypoperfusion injury for 15, 22.5 and 30 minutes. The cortical EEG and impedance of the foetal sheep was continuously recorded and the white matter analysed by histopathological methods for the presence of injury. At this gestational age, neurogenesis is largely complete (Barlow Russell McVeagh 1969 The foetal sheep: Morphogenesis of the nervous system and histochemical aspects of myelination. J Comp Neurol 135:249–262 Patterson D S P, Sweasey D, Herbert C N 1971 Changes occurring in the chemical composition of the central nervous system during foetal and post-natal development of the sheep. J Neurochem 18:2027–2040, and the cerebral sulci begin to develop and in man this occurs between 26 and 28 weeks. The cortical component of auditory and somatosensory evoked response becomes detectable at around 0.7 gestation, where as in man this occurs approximately 28 weeks of gestation (Hrbek A, Karlsson K, Kjellmer I, Olsson T, Riha M 1974 Cerebral reactions during intrauterine asphyxia in the sheep. II. Evoked electroencephalogram responses. Pediatr Res 8:58–63, Cook C J, Williams C E, Gluckman P D 1987 Brainstem auditory evoked potentials in the fetal lamb, in utero. J Dev Physiol 9:429–440. Cook C J, Gluckman P D, Johnston B M, Williams C E 1987 The development of the somatosensory evoked potential in the unanaesthetised fetal lamb. J Dev Physiol 9:441–456). Thus in terms of neural maturation the 0.65 gestation fetal sheep is highly comparable to the human between 24 and 32 weeks of gestation. During the 15 minute cerebral hypoperfusion injury an acute rise in cortical impedance (a measure of cytotoxic oedema) was measured, and a loss of spectral edge frequency in the EEG signal was observed—see FIGS. 1a, 2a and 4. In FIG. 2 100% on the vertical axis represents normal spectral edge frequency and amplitude. These features rapidly resolved after the hypoperfusion injury.

Figure 4B:
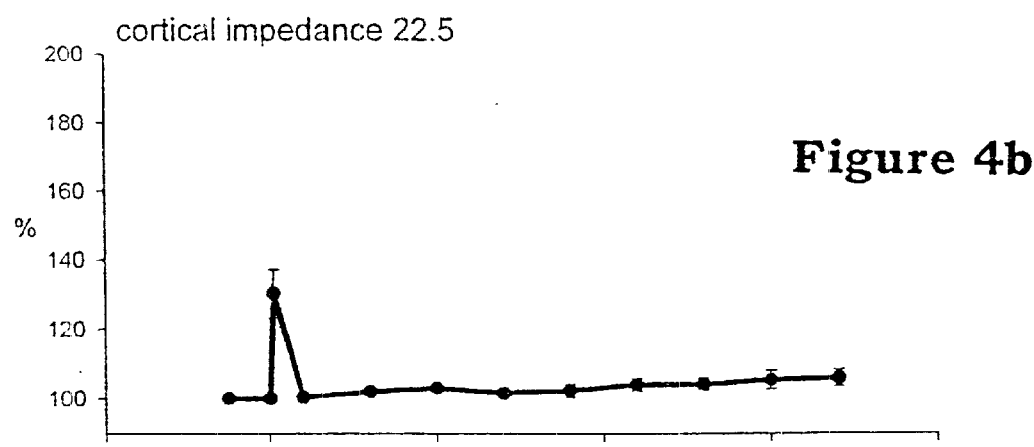
Figure 5A:
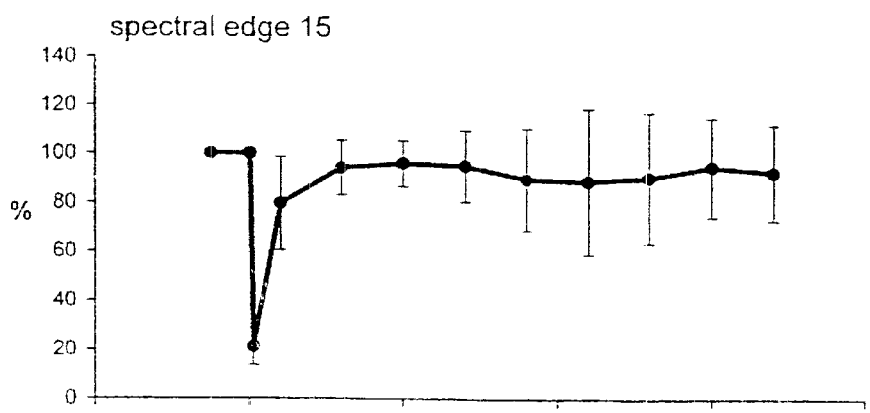
FIGS. 5a, 5b and 5c are graphs of EEG spectral edge frequency over the same 80 hour period.
Figure 5B:
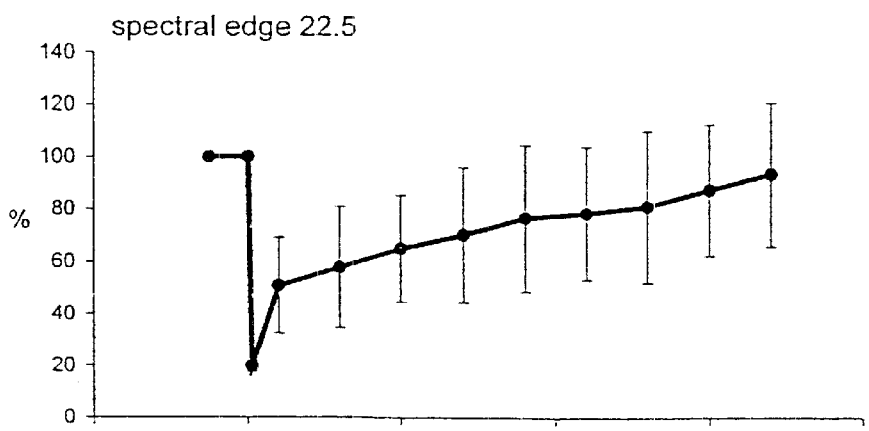
Figure 7A:
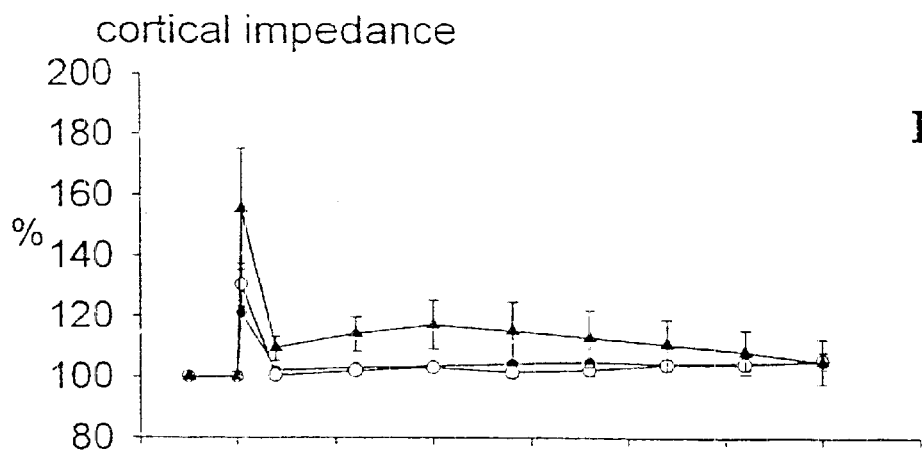
FIGS. 7a, 7b and 7c show the cortical impedance, EEG intensity, and spectral edge frequency plots each on the same axes, showing that the distinctive frequency response can be used to detect subtle (22.5 min) and severe white matter injuries (30 min)
Figure 7B:
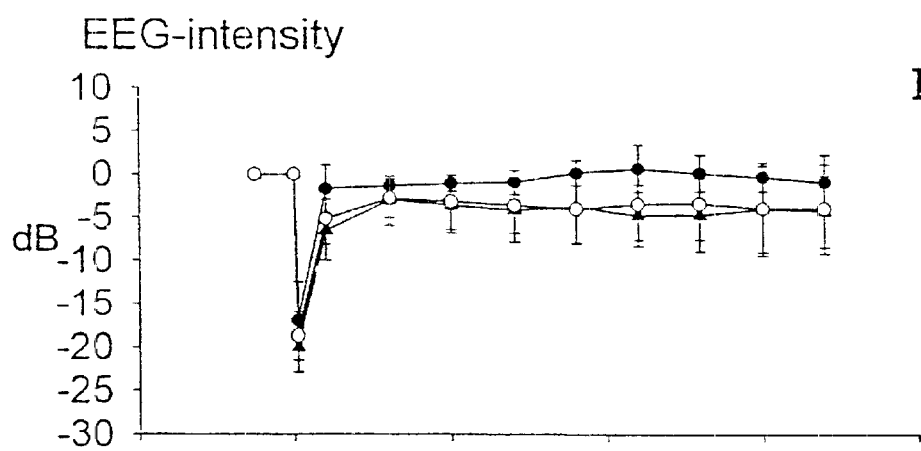
Figure 7C:
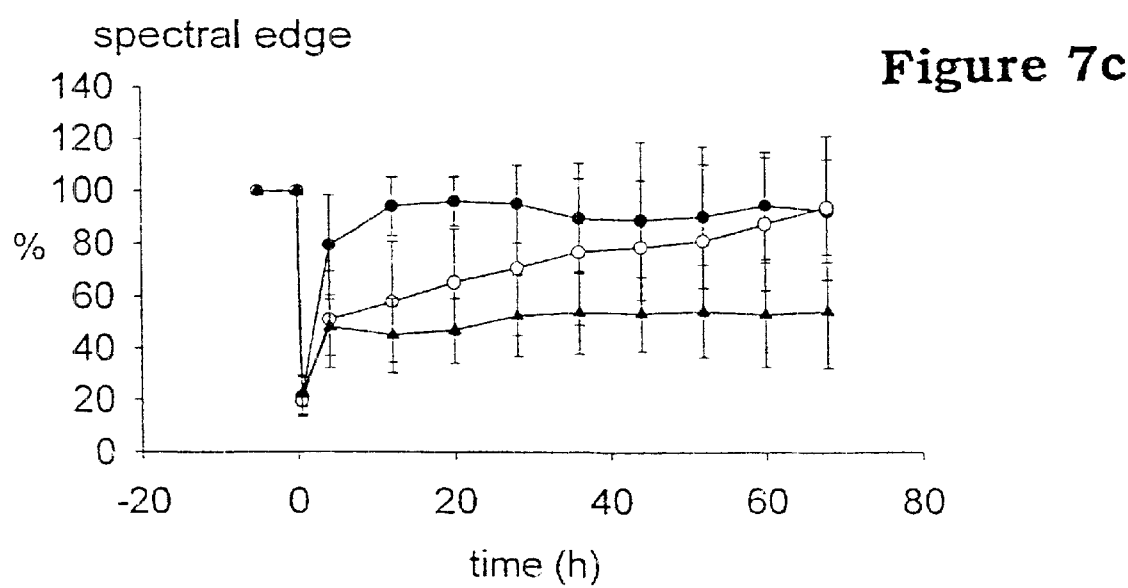

Following the 22.5 minute injury, there was a prolonged decrease in EEG spectral edge frequency—see FIGS. 4b, 5b and 7. Subsequently histopathologic analysis of the brain material showed gliosis in the corpus callosum and subcortical white matter which extended from the periventricular region dorsally and laterally. An equivalent type of 'subtle' injury is found in human infants, called telencephalic leukomalacia. The neurological outcome from this type of injury in humans is poor (Fujii et al., Pediatr Neurol., 9, 194–197, 1993). We believe that this loss of EEG spectral edge frequency is indicative of white matter injury.

Figure 4C:
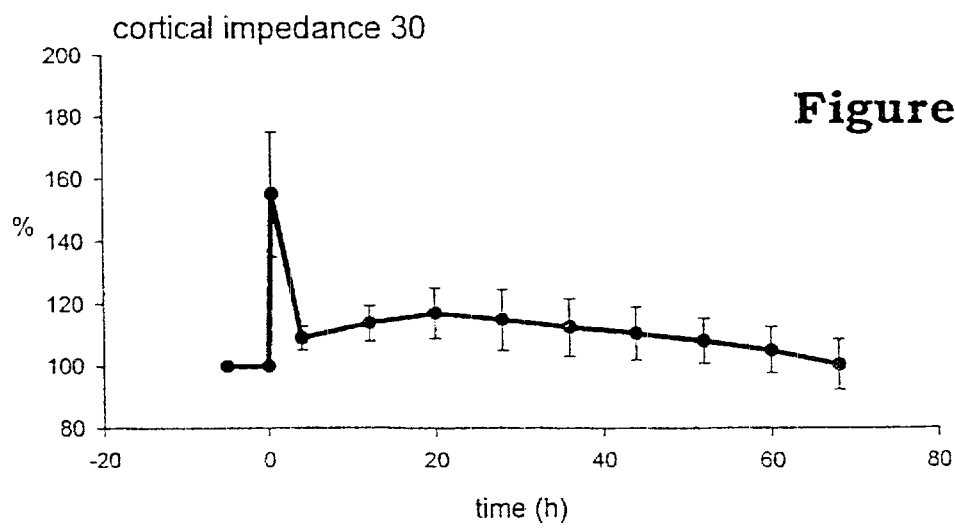
Figure 5C:
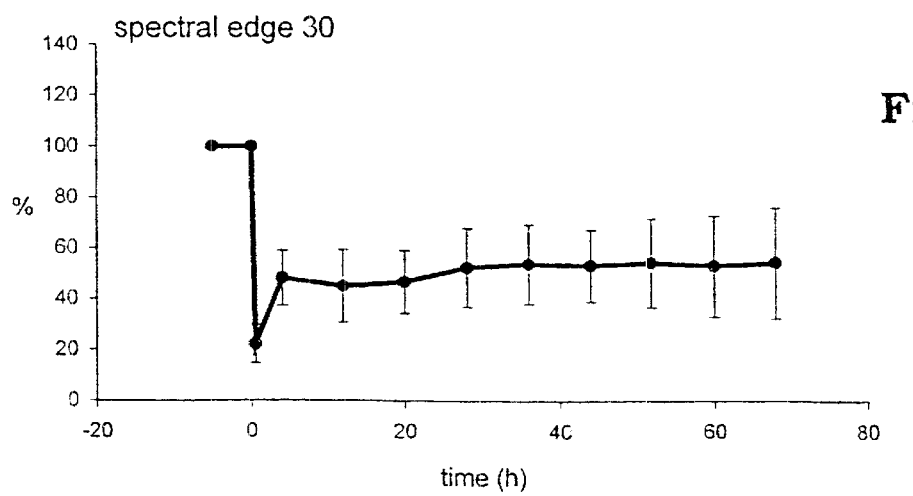
Figure 6A:
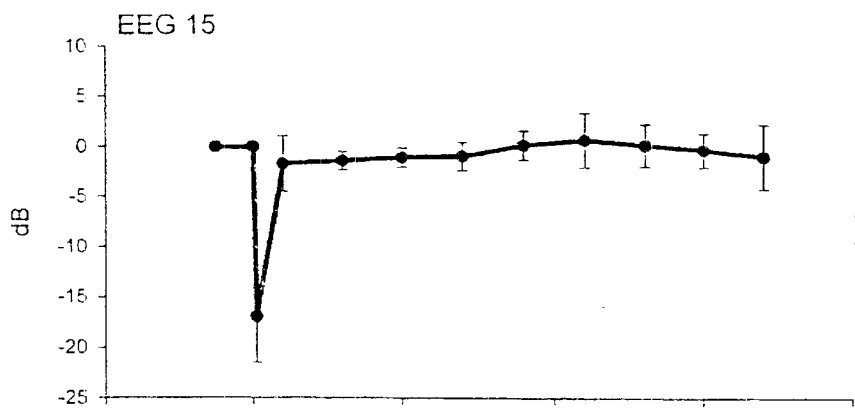
FIGS. 6a, 6b and 6c show EEG intensity taken over the same 80 hour period.
Figure 6B:
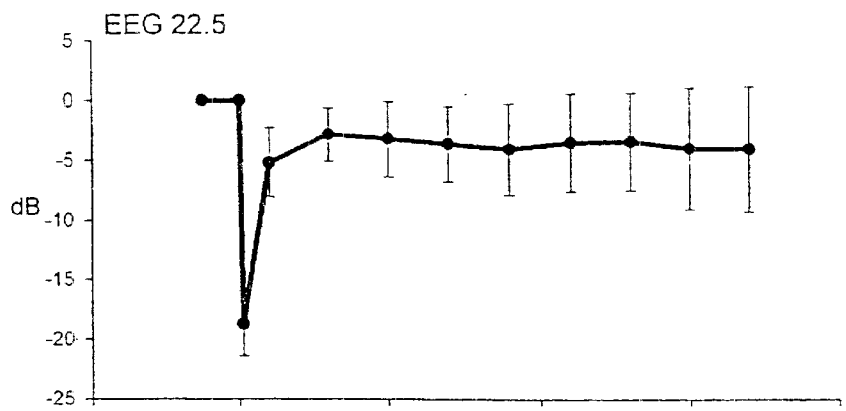
Figure 6C:
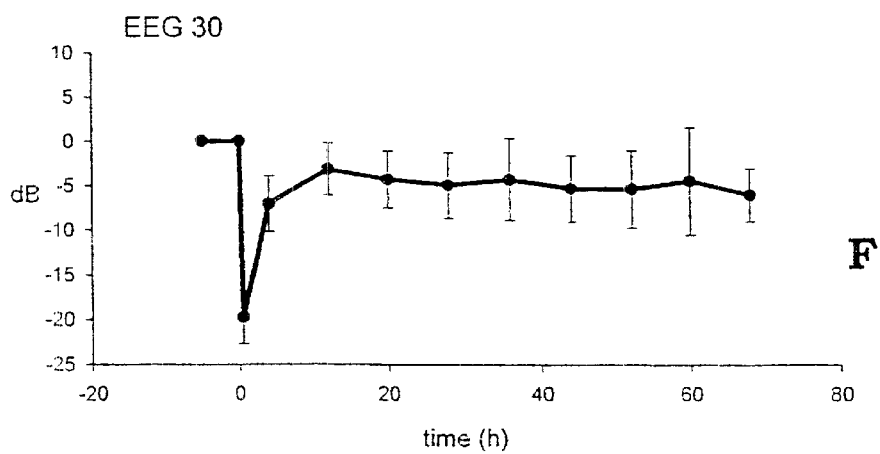

Following the 30 minute injury a secondary rise in impedance occurred with nonrecovery of spectral edge associated with severe white matter cystic infarction see FIGS. 4c, 6c and 7. Spectral edge activity in the EEG signal was permanently reduced to only around 50% of normal—see FIG. 5c. We believe this long term loss of spectral edge frequency is indicative of low long term neurological outcome. The term given to the equivalent type of white matter injury in the human infants is periventricular leukomalacia.

FIGS. 6a, 6b and 6c show a transient loss of EEG intensity in each case. At the onset of diminished blood perfusion there was a rapid loss of EEG intensity and while the recovery time to return to pre-injury EEG intensity was longer in the 30 minute injury compared with the 15 minute injury, the final outcome for the 3 durations of injury was the same.

FIG. 7 clearly demonstrates that both white matter gliosis and cystic infarction was associated with a prolonged loss of EEG frequency as indicated by the spectral edge data. In contrast the measures of the intensity (or similar measures such as power or amplitude) of the EEG were much less useful for detecting these white matter injuries following an insult.

Figure 8:
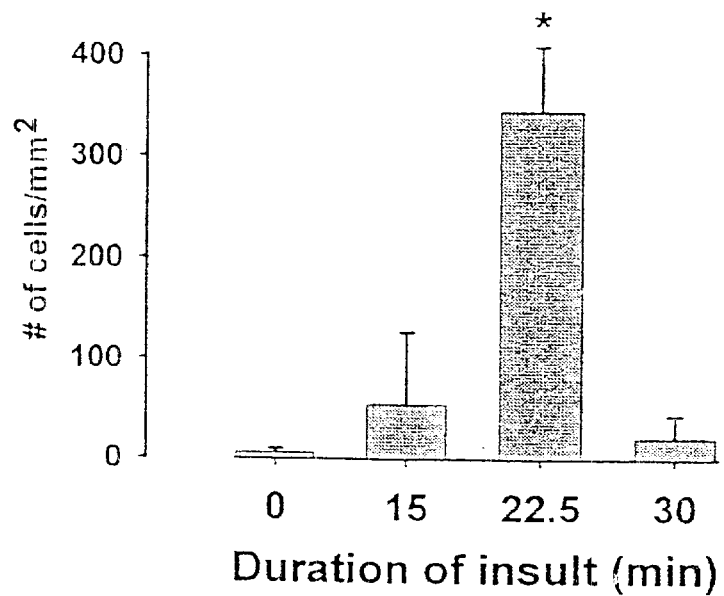
FIG. 8 is a graph comparing the density of GFAP positive cells in the subcortical white matter following different durations of ischemic injury.

FIG. 8 is a graph comparing the density of GFAP positive cells in the subcortical white matter following different durations of ischemic injury. The density of these cells was determined in the frontoparietal cortex dorsolateral to the external angle of the lateral ventricle. There was only a mild (non significant) response in the 15 minute group. There was a marked increase in the number of GFAP positive cells in the 22.5 minute group (p<0.05). After the 30 minute injury, the GFAP response was less than the 22.5 minute group. This lesser induction in the 30 min group reflects the presence of extensive cell death within the same region. Kruskall Wallis ANOVA on ranks. The marked increase in the number of cells (GFAP) after the 22.5 min injury is indicative of a 'subtle' injury to the white matter tracts.

Figure 9:
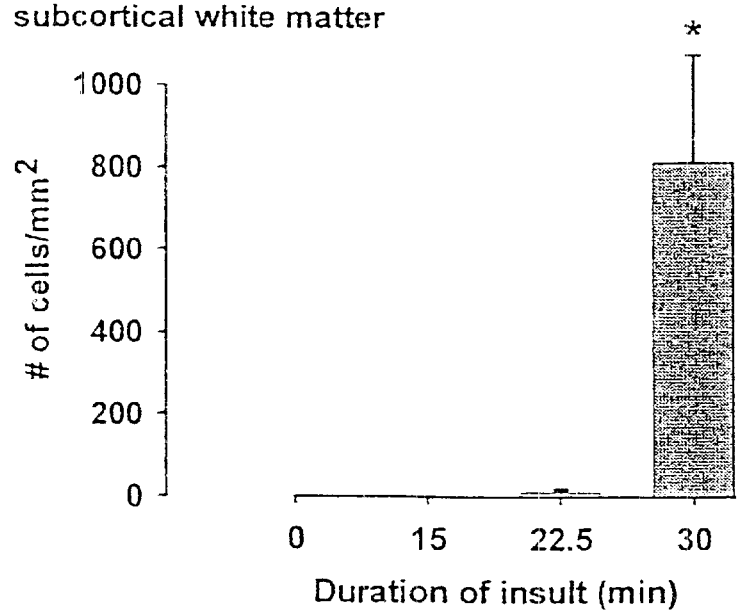
FIG. 9 is a graph comparing the density of TUNEL positive cells in the subcortical white matter following the same different durations of ischemic injury.

FIG. 9 is a graph comparing the density of TUNEL positive cells in the subcortical white matter following the different durations of ischemic injury. The density of these cells was determined in the region dorsal and lateral to the external angle of the lateral ventricle. There was a significant increase of TUNEL positive cells only after the 30 minute injury. This cell loss reflects the development of a severe or cystic white matter lesion.

Figure 10A:
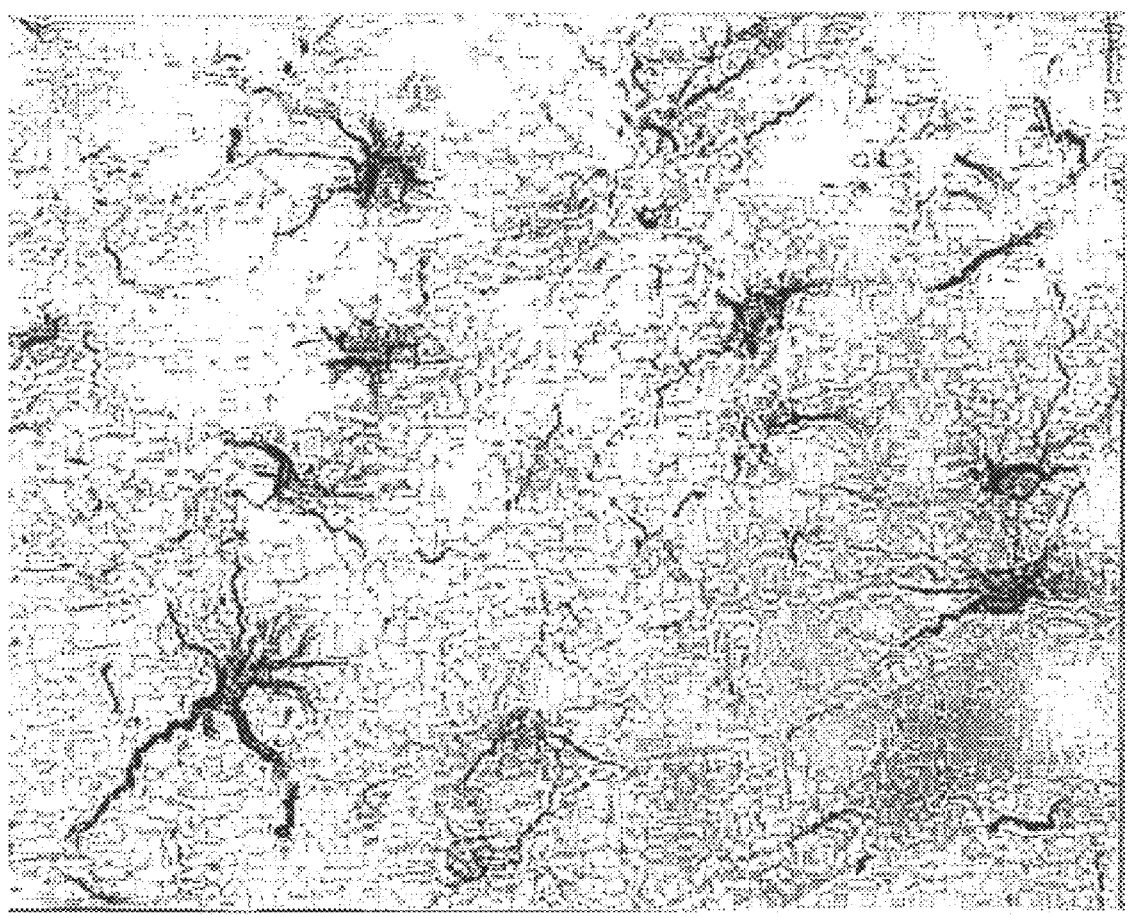
FIGS. 10a and 10b are illustrations of the diffuse glial (GFAP) reaction in the white matter of the parietal cortex following the 22.5 minutes of ischemia injury and from an age matched control, respectively.
Figure 10B:
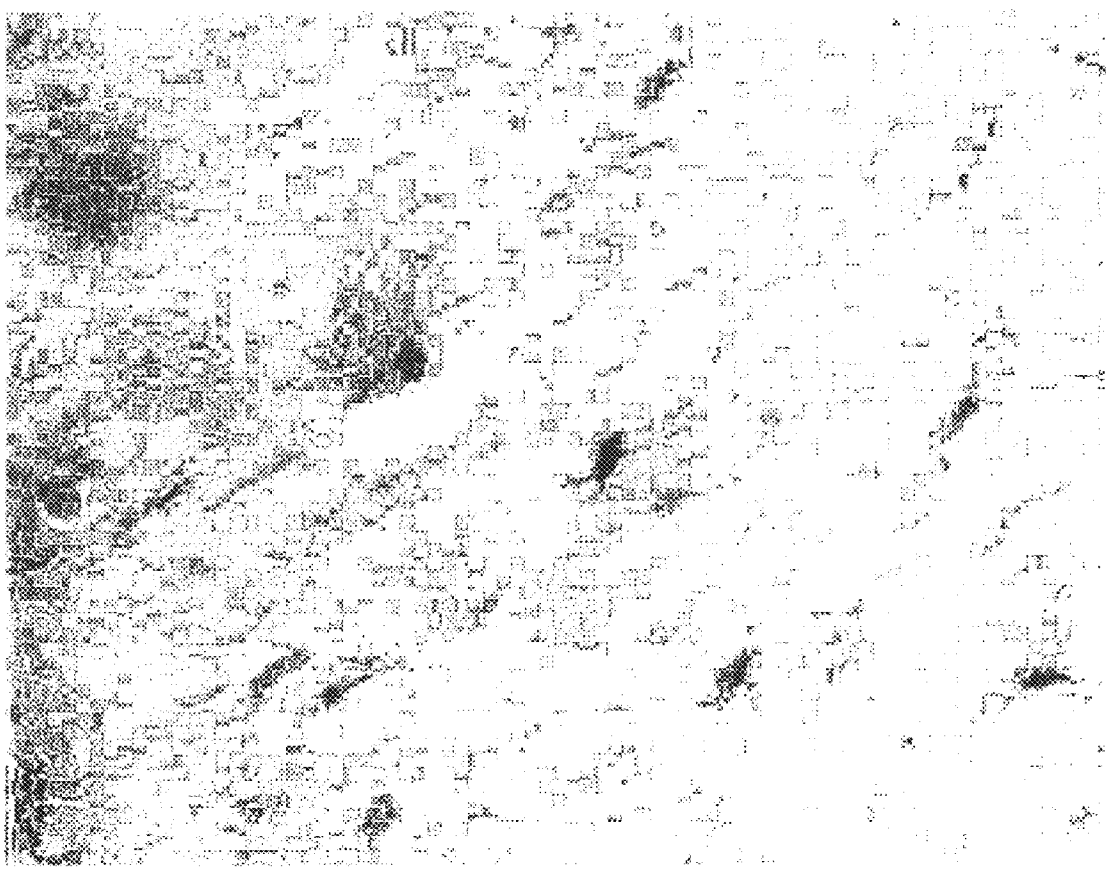

FIGS. 10 and 10b are illustrations of representative examples of the diffuse glial (GFAP) reaction in the white matter of the parietal cortex following the 22.5 minutes of ischemia injury and from an age matched control. Note that the GFAP positive cells in the 22.5 minute group have a morphology typical of hypertrophic or reactive astrocytes (lower left). Brown stain is GFAP immunoreactivity. Bar= 100 $\mu$m. This reaction is typical of a 'subtle' white matter injury.

Thus, we believe that loss or reduction of activity in the upper portion or spectral edge of the EEG frequency domain particularly in the immature brain is predictive of neural dysfunction, while EEG intensity is not. Furthermore, non-recovery of spectral edge frequency is predictive of the type of neural injury that has occurred.

The foregoing describes the invention including preferred forms thereof. Alterations and modifications as will be obvious to those skilled in the art are intended to be incorporated within the scope hereof as defined in the claims.

What is claimed is:

1. A method for early prediction of neural damage or neurological outcome for an infant born prematurely, comprising:
    acquiring EEG signal(s) from the surface of the head of the infant,
    analysing the frequency distribution or content of the signal(s) to determine the frequency range in which a major portion of the EEG activity in the frequency domain occurs or a frequency below which a major portion of the EEG activity occurs, and
    predicting neural damage or neurological outcome for the infant based on EEG activity or loss thereof in the upper part of the frequency range.

2. A method according to claim 1 including comparing the analysed data with stored comparative spectral edge and neurological outcome information for infants born prematurely.

3. A method according to claim 1 including acquiring the EEG signal(s) over a number of hours.

4. A method according to claim 1 including acquiring the EEG signal(s) over one or more days.

5. A method according to claim 1 including averaging the EEG signal(s) acquired over a number of hours or one or more days.

6. A method according to claim 1 including analysing the EEG signals in the frequency domain for loss of EEG activity above about 10 Hz.

7. A method according to claim 1 including analysing the EEG signals in the frequency domain for loss of EEG activity above about 8 Hz.

8. A method according to claim 1 including determining the frequency below which about 90% of the EEG activity in the frequency domain occurs.

9. A method according to claim 1 including determining the frequency below which about 95% of the EEG activity in the frequency domain occurs.

10. A method according to claim 1 wherein the EEG signals are acquired from electrodes placed on the infants head over the parasagittal region/fronto-parietal-occipital cortex.

11. A method according to claim 1 including applying to the infant therapy against the development of white matter injury after detecting any loss of EEG activity in the upper part of the frequency range.

12. A method according to claim 1 wherein said neural damage is telencephalic leukomalacia or periventricular leukomalacia.

13. A system for early prediction of neural injury or neurological outcome for an infant born prematurely, comprising:
    means for acquiring EEG signal(s) from the surface of the head of the infant, and
    computing means arranged to analyse the frequency distribution or content of the signal(s) to determine the frequency range in which a major portion of the EEG activity in the frequency domain occurs or a frequency below which a major portion of the EEG activity occurs, and to compare the analysed data with stored comparative EEG frequency and neural damage or neurological outcome information for infants born prematurely and produce output information predictive of neural damage or neurological outcome for the infant based on EEG activity or loss thereof in the upper part of the frequency range.

14. A system according to claim 13 arranged to analyse EEG signal(s) acquired over a number of hours.

15. A system according to claim 13 arranged to analyse EEG signal(s) acquired over one or more days.

16. A system according to claim 14 arranged to average the EEG signal(s) acquired over a number of hours or one or more days.

17. A system according to claim 13 arranged to analyse the EEG signals in the frequency domain for activity above 10 Hz.

18. A system according to claim 13 arranged to analyse the EEG signals in the frequency domain for activity above 8 Hz.

19. A system according to claim 13 to arranged to determine the frequency below which about 90% of the EEG activity in the frequency domain occurs.

20. A system according to claim 13 arranged to determine the frequency below which about 95% of the EEG activity in the frequency domain occurs.

* * * * *